US011033866B2

(12) United States Patent
Sattig et al.

(10) Patent No.: US 11,033,866 B2
(45) Date of Patent: Jun. 15, 2021

(54) MIXING DEVICE FOR BONE CEMENT

(71) Applicant: OSARTIS GmbH, Dieburg (DE)

(72) Inventors: Christoph Sattig, Dieburg (DE); Ingeborg Liedtke, Muenster (DE)

(73) Assignee: OSARTIS GmbH, Münster (DE)

(*) Notice: Subject to any disclaimer, the term of this patent is extended or adjusted under 35 U.S.C. 154(b) by 0 days.

(21) Appl. No.: 15/217,544

(22) Filed: Jul. 22, 2016

(65) Prior Publication Data
US 2017/0028369 A1 Feb. 2, 2017

(30) Foreign Application Priority Data
Jul. 27, 2015 (DE) .................. 10 2015 112 203.0

(51) Int. Cl.
| B01F 15/02 | (2006.01) |
| B01F 11/00 | (2006.01) |
| A61B 17/88 | (2006.01) |
| B01F 7/00 | (2006.01) |
| B01F 13/00 | (2006.01) |
| B01F 15/00 | (2006.01) |
| B05C 17/005 | (2006.01) |

(52) U.S. Cl.
CPC ...... B01F 15/0278 (2013.01); A61B 17/8833 (2013.01); B01F 7/0025 (2013.01); B01F 11/0082 (2013.01); B01F 13/0023 (2013.01); B01F 15/00779 (2013.01); B01F 15/00831 (2013.01); B01F 15/0235 (2013.01); B01F 15/0279 (2013.01); B05C 17/00576 (2013.01); B05C 17/00593 (2013.01); *A61B 2017/8838* (2013.01); *B01F 2215/0029* (2013.01)

(58) Field of Classification Search
CPC .............. B01F 15/0278; B01F 11/0082; B01F 13/0023; B01F 15/0279; A61B 17/8833; A61B 2017/8838; B05C 17/00593
USPC .......................................................... 366/189
See application file for complete search history.

(56) References Cited

U.S. PATENT DOCUMENTS

| 6,379,033 B1 * | 4/2002 | Murray ................. B01F 3/1228 366/139 |
| 2008/0304355 A1 * | 12/2008 | Sattig ................. A61B 17/8825 366/133 |
| 2012/0132675 A1 * | 5/2012 | Vogt ................... A61B 17/8825 222/327 |

(Continued)

FOREIGN PATENT DOCUMENTS

| CN | 102551871 A | 7/2012 |
| CN | 103801216 A | 5/2014 |
| DE | 102007026034 A1 | 12/2008 |

(Continued)

OTHER PUBLICATIONS

Officer: Den Haag, "European Search Report", European Patent Application No. EP 16 18 0536, dated Jan. 2, 2017, p. 3 Published in: EP.

(Continued)

*Primary Examiner* — Marc C Howell
(74) *Attorney, Agent, or Firm* — Kaplan Breyer Schwarz, LLP

(57) ABSTRACT

A mixing device for bone cement comprising a plunger for extruding the mixed material, which plunger is also used as a cover. The plunger has spring blades adapted to be latched on a collar of the housing.

14 Claims, 11 Drawing Sheets

(56) References Cited

U.S. PATENT DOCUMENTS

2014/0126320 A1* 5/2014 Vogt .................... B29B 7/80
                                                366/76.7
2015/0320935 A1* 11/2015 Dungar ................ A61M 5/284
                                                604/91

FOREIGN PATENT DOCUMENTS

| DE | 102012024710 A1 | 5/2014 |
| EP | 2457531 A1 | 5/2012 |
| WO | 2005048867 A2 | 6/2005 |

OTHER PUBLICATIONS

Office Action issued in corresponding Chinese patent application No. 201610891809.7, dated May 7, 2020, 28 pp.

* cited by examiner

MIXING DEVICE FOR BONE CEMENT

FIELD OF THE INVENTION

The invention relates to a mixing device, more particularly to a mixing device such as employed for mixing bone cement.

BACKGROUND OF THE INVENTION

Bone cements, especially polymer-based bone cements, are usually made from a powder component and a liquid component. For mixing the bone cement, usually a mixing device is used which comprises a mixing cavity in which the powder component and the liquid component are mixed to give a readily processible pasty mass.

A mixing device for bone cement is known from DE 10 2007 026 034 A1 (aap Biomaterials GmbH & Co. KG).

This mixing device comprises a plunger which serves as a cover of the mixing cavity during mixing and in which a rod with a grip for moving the mixing paddle is guided.

After mixing, the rod is broken off and by means of an applicator gun the plunger can then be moved forward by increased force and can so fulfill its proper function as a plunger for forcing out the bone cement. Such a device is an easy to use one-way system.

In order to secure the plunger in a first position as a cover and to allow the plunger to be pressed forward from this position with increased force, a latching ring is provided between the plunger and the housing.

SUMMARY OF THE INVENTION

Given this background, the invention is based on the object to further improve a mixing device for bone cement as described above in terms of its assembly, manufacturing, and/or handling.

In particular it should be made possible to provide a plunger that can be used as a cover and which does not require any additional component for this purpose.

The object of the invention is achieved by a mixing device according to the illustrative embodiment of the present invention.

The invention relates to a mixing device which is in particular adapted for mixing bone cement.

The mixing device comprises a housing with a mixing cavity. The mixing cavity usually has a circular cylindrical shape.

Moreover, the mixing device comprises a plunger for extruding the mixed material, which plunger serves as a housing cover during mixing of the material to be mixed.

Preferably, a rod with a grip for moving a mixing paddle is guided in the plunger.

Once the material to be mixed has been mixed, the plunger can be moved out of the position where it is used as a cover by applying a force and then serves to force out the mixed material.

According to the invention, the plunger comprises a plurality of spring blades which are adapted to be latched on a collar of the housing and to release the plunger when a force is applied to the plunger.

It has been found that spring blades directly arranged on the plunger, in particular spring blades that are formed integrally with the plunger or a portion of the plunger permit to provide a latching mechanism which on the one hand allows to reliably secure the plunger in a first position as a cover, and on the other hand to move the plunger out of this cover position by a defined increased force in order to serve as a plunger.

For this purpose, the plunger is moved forward together with the spring blades. In the context of the invention, forward means the direction in which the plunger is moved to force out the mixed material.

This allows to dispense with further components for providing the latching mechanism, thereby facilitating manufacturing and also assembly and handling and making them safer and more reliable.

The collar is in particular formed as a circumferential engagement surface which extends around the entire inner circumference of the housing. Preferably, the collar has no interruptions. The engagement surface of the collar preferably extends perpendicular to the central axis of the plunger.

The plunger preferably has at least 4, more preferably at least 8, and most preferably at least 12 spring blades.

In a preferred embodiment the spring blades are at least partially locked below one or more locking hooks of the housing when the plunger is in the position in which it serves as a cover. At the same time the spring blades have an opposite engagement surface which engages on a corresponding support surface of the collar of the housing.

The collar which serves to accommodate the plunger in its cover position therefore defines a forward stop with its support surface. A rearward stop is ensured by the latched position of the spring blades below a locking hook of the housing.

The one or more locking hook(s) preferably have an inclined sliding surface on the upper side thereof to make it easy for the spring blades to snap into place when the plunger is assembled.

The locking hooks preferably form an integral part of the housing that defines the mixing cavity, by being integrally formed therewith.

The one or more locking hooks preferably cover a smaller circumferential portion than the spring blades, that is to say they are distributed over sections around the collar of the housing.

A result easily achieved in this manner is that the plunger can be latched in its cover position with significantly less force than is required to move the plunger further forward.

The spring blades are preferably L-shaped.

In particular it is contemplated that the spring blades have a spring portion which is inclined with respect to a central axis of the plunger, in particular at an angle between 10° and 60°. An improvement brought about thereby is that the plunger can be moved forward with substantially constant force even in case of manufacturing tolerances.

Furthermore, the spring blades have an outer hook portion preferably extending substantially horizontally or slightly inclined. In the cover position, this hook portion engages on a support surface of the collar while being locked behind at least one locking hook.

In one embodiment of the invention, the plunger has a front portion that has an enlarged diameter with respect to a rearward portion. In this manner, a sealing effect is already obtained at the very front of the plunger and at the same time the plunger is guided.

Behind the enlarged front portion a further enlarged portion is preferably provided, where the plunger engages the wall of the mixing cavity. This may especially be an elastomeric seal, such as e.g. an O-ring recessed in a groove of the plunger. In this manner the plunger is reliably guided by at least two axially spaced engaging portions.

The spring blades are preferably arranged rearwards as seen in the movement direction of the plunger.

In one embodiment of the invention, a funnel can be placed on the housing of the mixing device, which funnel is divided into two areas, for example by a partition.

One area may serve for filling the liquid component and a further area for filling the powder component.

BRIEF DESCRIPTION OF THE DRAWINGS

The subject matter of the invention will now be described in more detail below by way of an exemplary embodiment illustrated in the drawings of FIG. 1 to FIG. 11.

DETAILED DESCRIPTION

Figure 1:
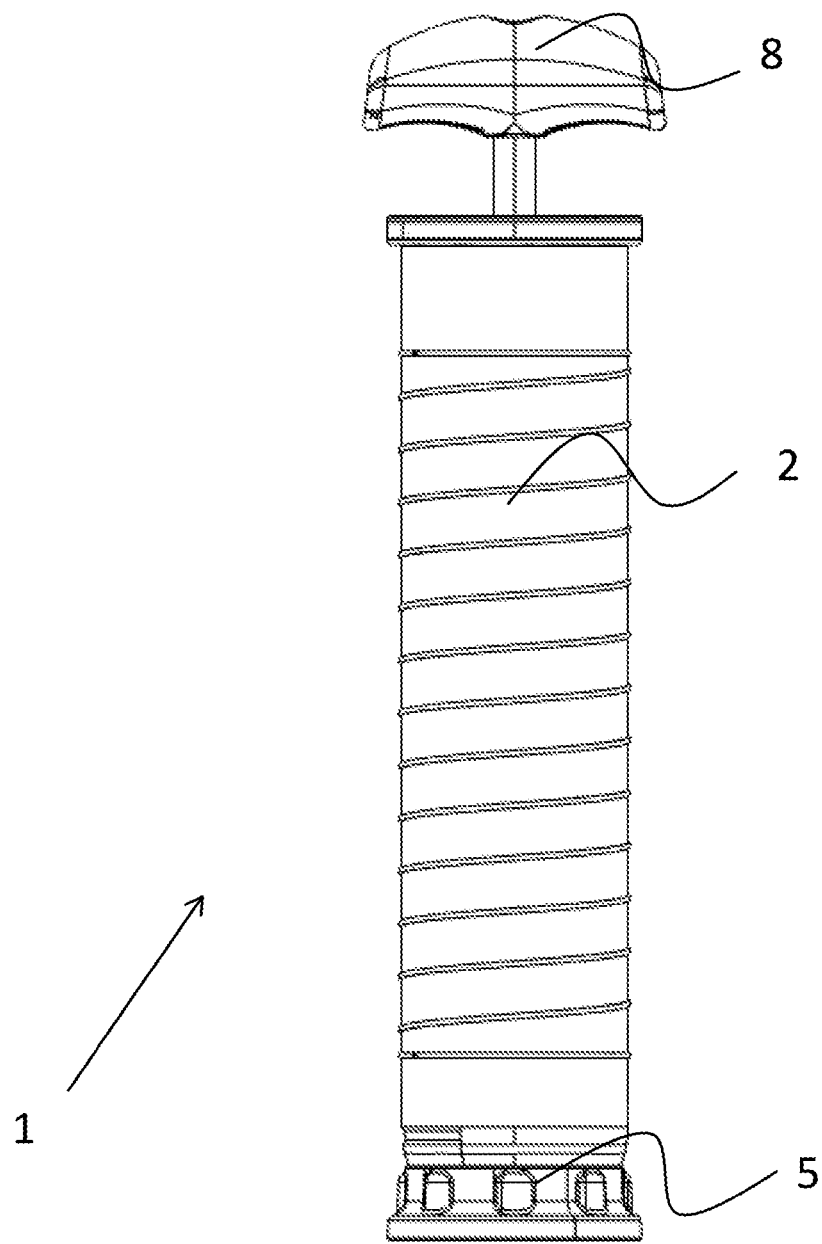
FIG. 1 shows an elevational side view of a mixing device.

FIG. 1 shows an elevational side view of a mixing device 1.

Mixing device 1 comprises a housing 2 which substantially has a circular cylindrical shape and serves to accommodate the material to be mixed.

The housing has a bottom 5 which is detachable, in particular by being screwed off, for mounting an application tube. The latter may be attached by screwing for example after mixing of the bone cement.

An underside of bottom 5 is planar thereby defining a footprint for the mixing device 1.

The material to be mixed can be mixed by actuating a mixing paddle using grip 8.

Figure 2:
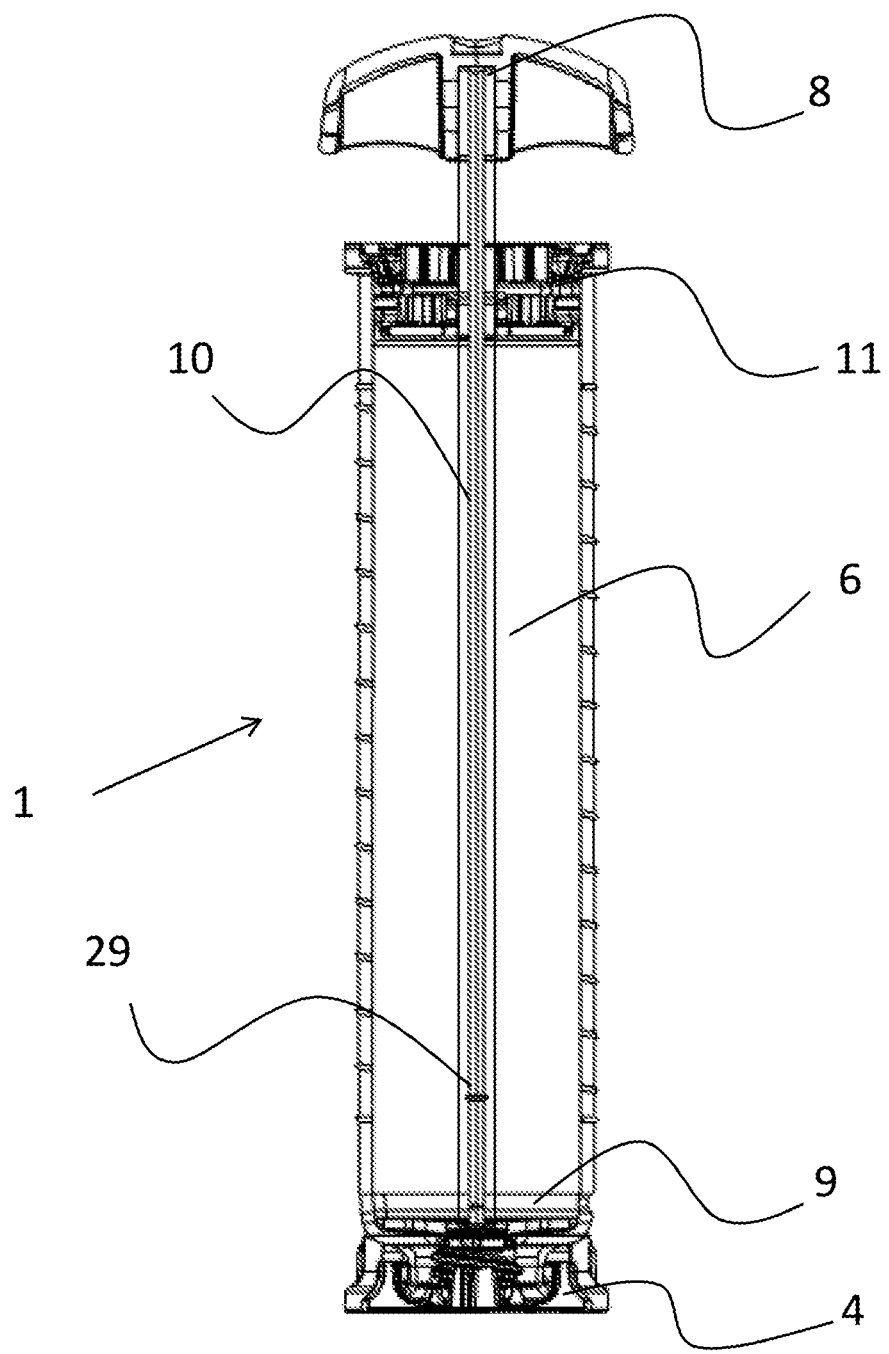
FIG. 2 is a sectional view of the mixing device illustrated in FIG. 1.

FIG. 2 is a sectional view of the mixing device 1 shown in FIG. 1. Here the circular cylindrical mixing cavity 6 can be seen.

In the here illustrated position, a plunger 11 which serves to force out the mixed material is used as a cover prior to the mixing of the material to be mixed.

A rod 10 for driving a mixing paddle 9 is guided in plunger 11. Rod 10 and hence mixing paddle 9 can be moved by means of grip 8.

Mixing device 1 may be utilized as follows:

After introducing the material to be mixed into mixing cavity 6, the plunger 11 together with the mixing paddle 9 guided on rod 10 is assembled. By moving the mixing paddle 9 using grip 8 the material to be mixed is mixed.

Then grip 8 is retracted.

The grip can be removed together with the rod.

For this purpose, the rod has a predetermined breaking point 29.

Mixing device 1 may then be inserted into an applicator gun (not shown), and after removal of bottom 5 the mixed material can then be forced out using a screw-connected application tube 4 by urging the plunger 11 forward using the applicator gun.

Figure 3:
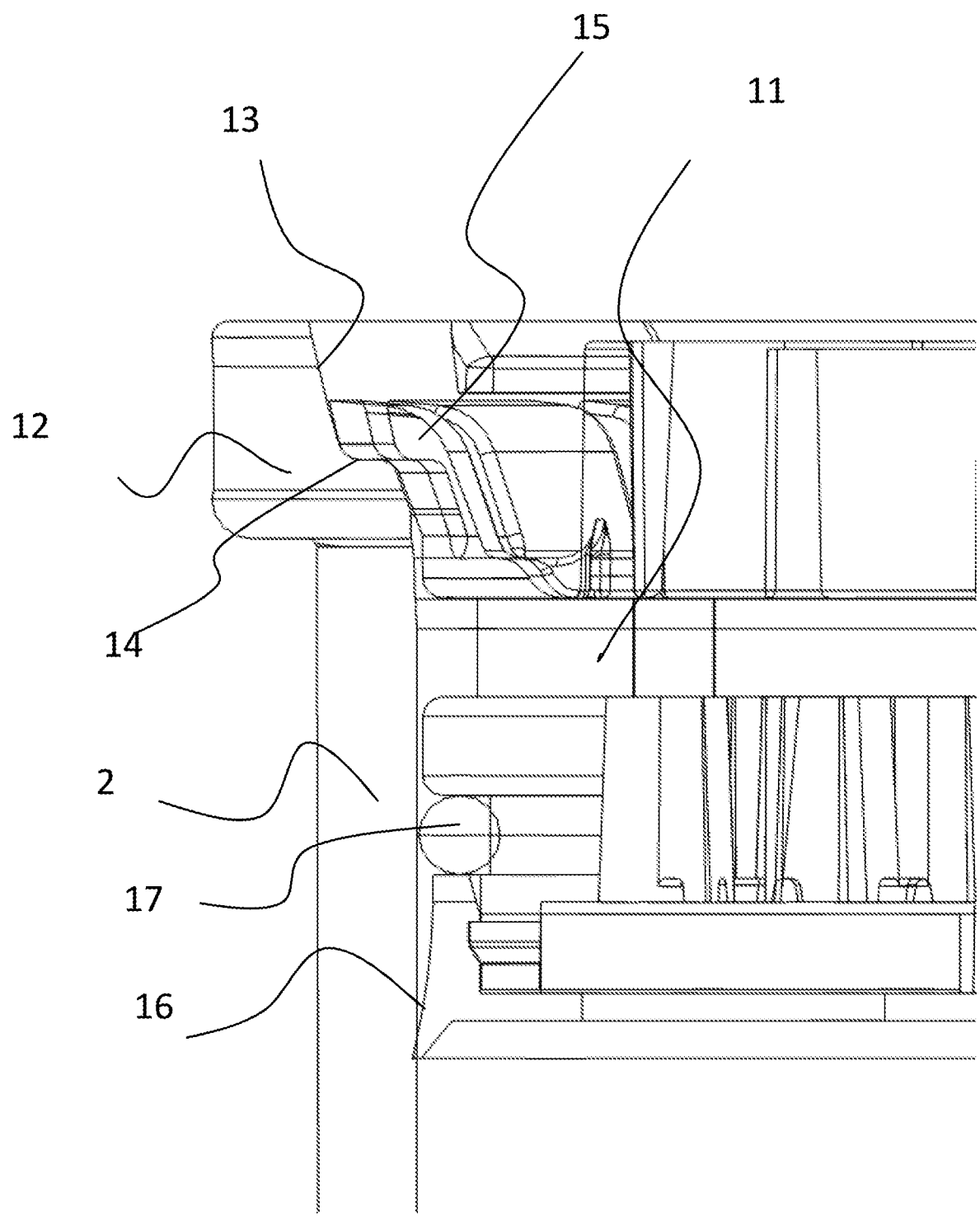
FIG. 3 is a view of a detail of a sectional view of the collar portion of the mixing device.

FIG. 3 shows a sectional view of a detail of the collar portion of the mixing device.

It can be seen that the collar 12 has an inclined surface 13.

Plunger 11 has substantially L-shaped spring blades 15.

In this figure, the cover position of plunger 11 is shown.

In this position, a substantially horizontally extending support surface 14 of the plunger defines a stop for the spring blades 15.

When an increased force is applied, the L-shaped spring blades 15 will resiliently deflect inwards and the plunger 11 can be moved forward.

In a front portion 16 the diameter of the plunger increases.

The front portion 16 is provided in form of a wiper attached on the rest of the plunger as a separate component, for example by snap-connection.

Behind front portion 16, a seal is recessed in a groove of plunger 11, for example an O-ring of elastomeric material.

In this way, the plunger is reliably guided in housing 2.

Spring blades 15 are formed integrally with the adjacent plunger 11. Thus, no separate component is required in order to secure the plunger in the cover position illustrated here.

Figure 4:
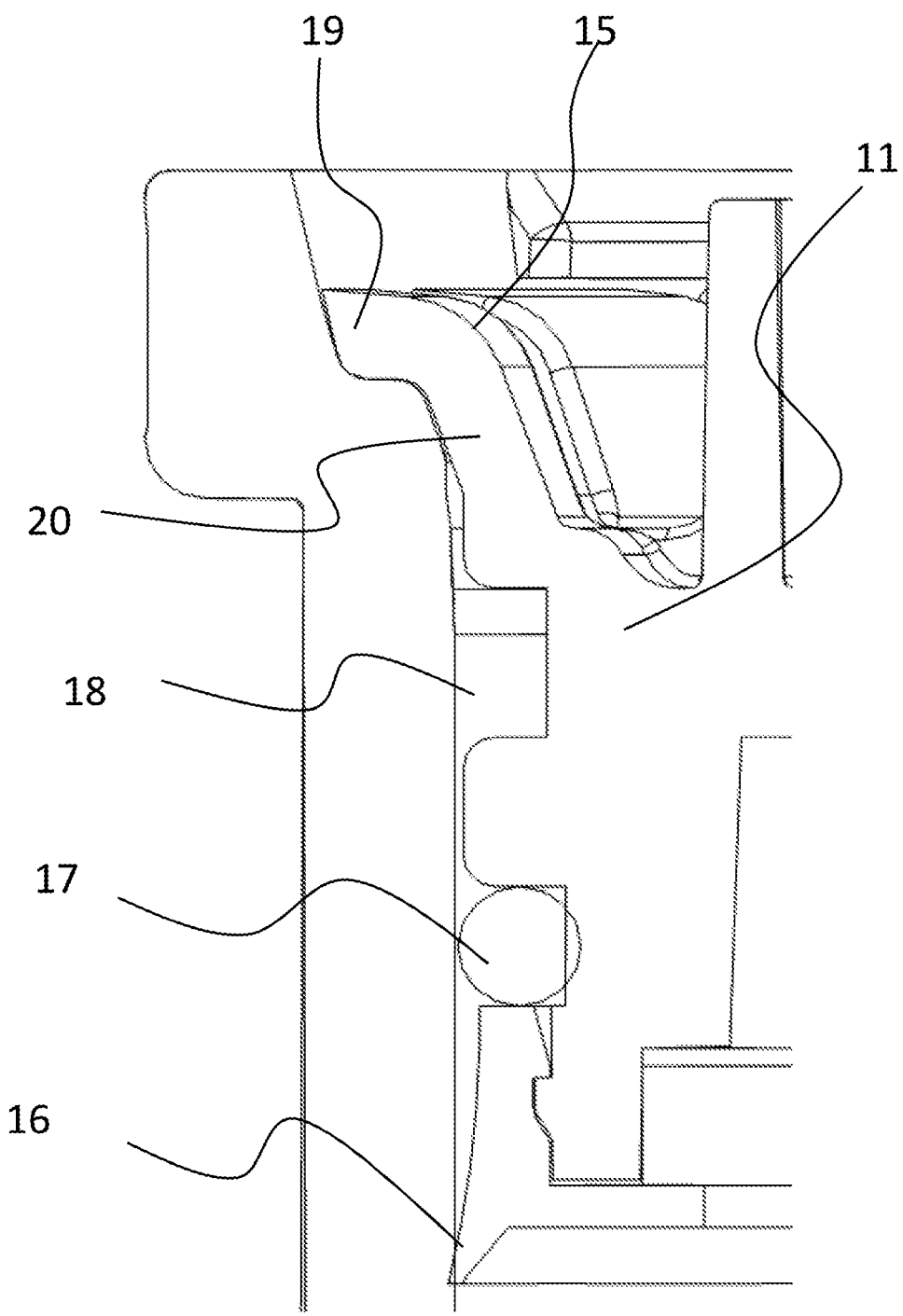
FIG. 4 is a schematic sectional view.

FIG. 4 shows a schematic sectional view of the collar portion. Here again, the front portion 16 with enlarged diameter of the plunger 11 can be seen, as well as the seal 17 rearwards thereof. Before plunger 11 merges into the L-shaped spring blades 15, it has a circumferential groove 18.

Spring blades 15 have a spring portion 20 and a hook portion 19 extending more horizontally than the spring portion.

Figure 5:
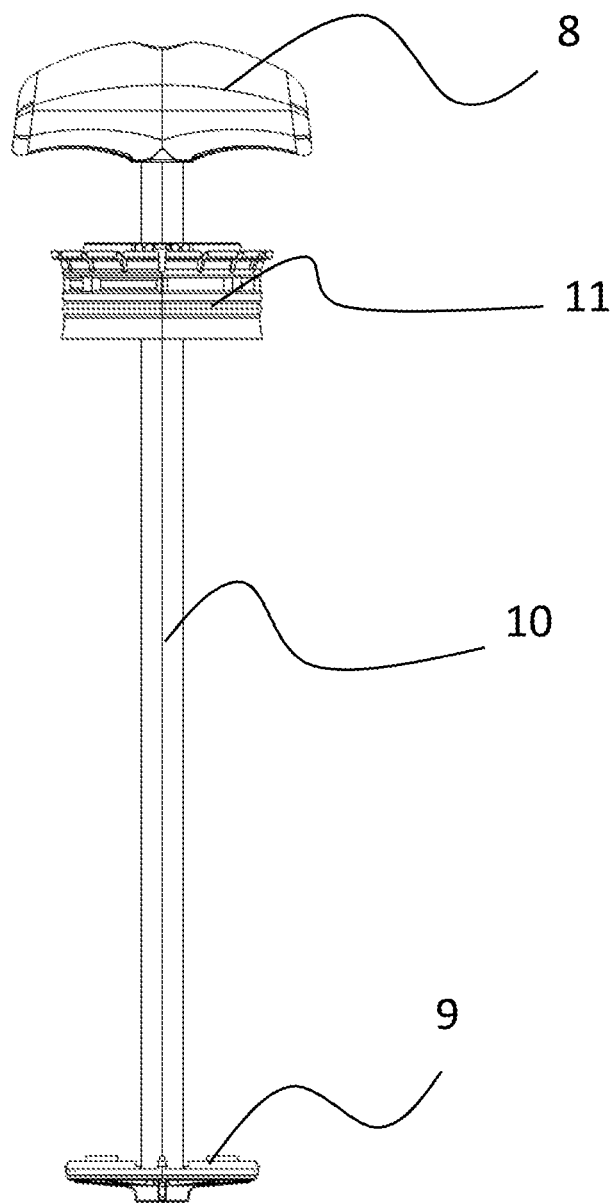
FIG. 5 is an elevational side view of the plunger and of a mixing paddle with grip guided in the plunger.

FIG. 5 is side elevational view of plunger 11 with the rod 10 with mixing paddle 9 and grip 8 guided therein.

These components can be assembled once the material to be mixed has been introduced, optionally with the receiving cup (3 in FIG. 10), and plunger 11 serves as a cover.

Figure 6:
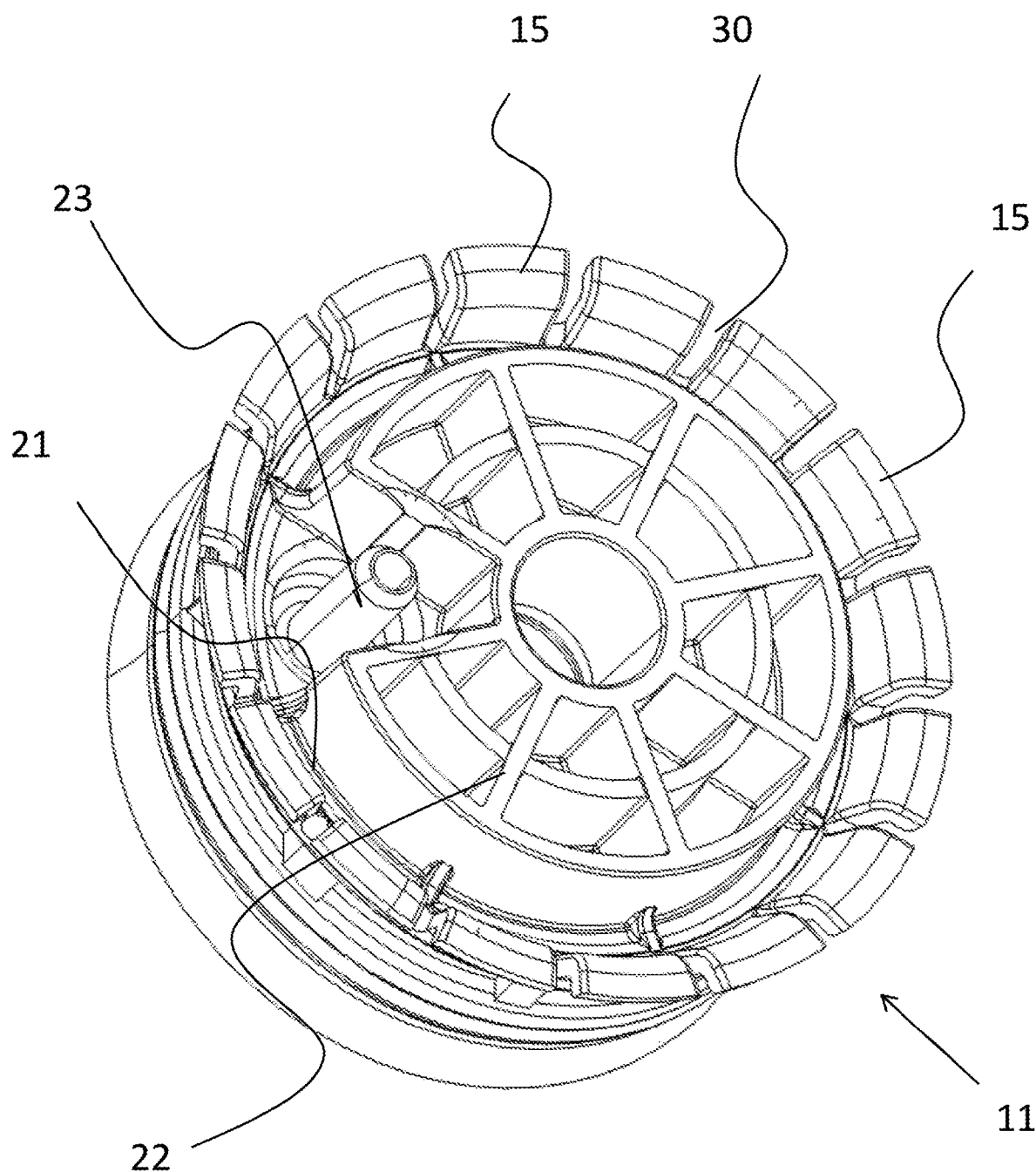
FIG. 6 is a perspective view of the plunger.

FIG. 6 shows a detailed view of plunger 11. Plunger 11 has a plurality of L-shaped spring blades 15. In the present exemplary embodiment, 16 spring blades are provided. Preferably, the plunger should have at least 6 spring blades.

To be able to resiliently deflect inwards, the spring blades are separated from one another by cuts 30.

The body of plunger 11 is in part defined by a lightweight structure 22 consisting of circumferential walls which are connected by webs.

Figure 10:
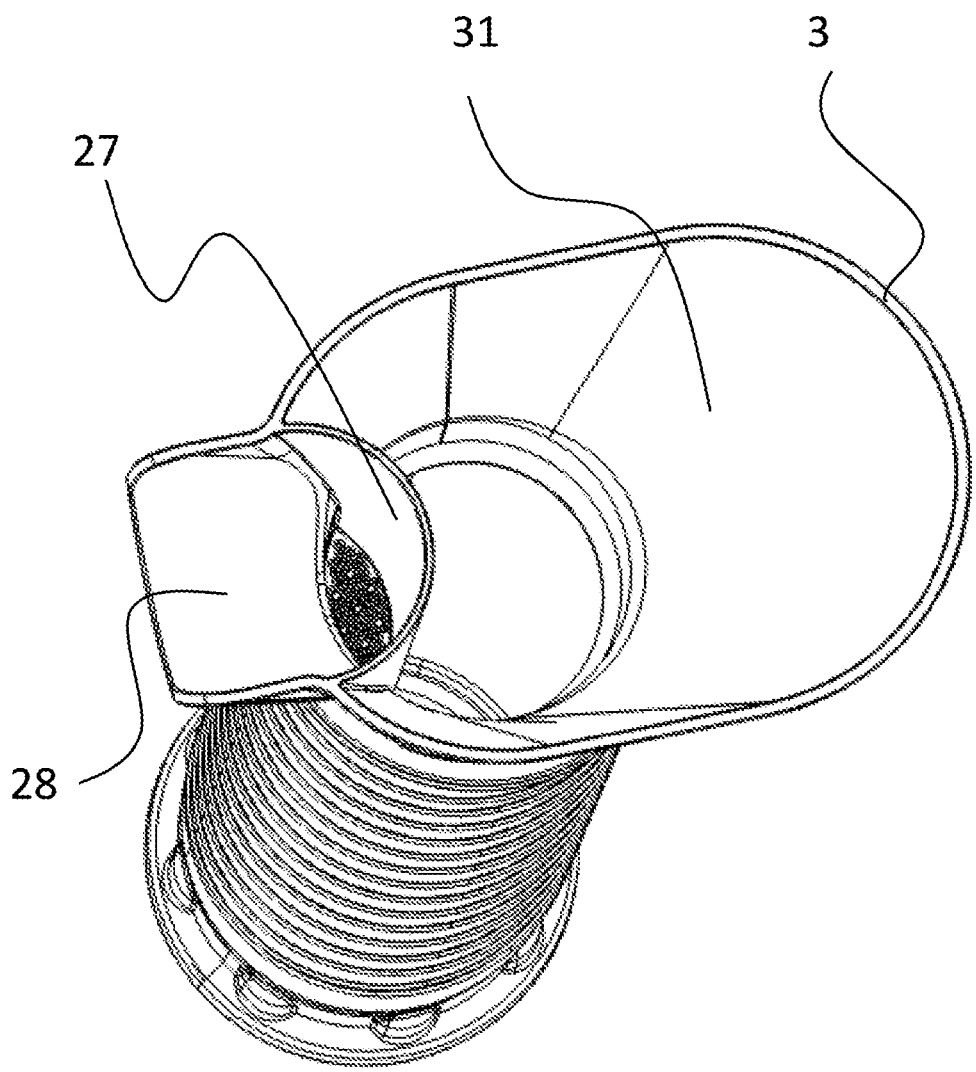
FIG. 10 is a perspective detailed view of the mixing device with a funnel placed thereon from above.

Moreover, plunger 11 has a circumferential groove 21 on its upper side which is used for inserting the receiving cup (3 in FIG. 10).

Furthermore, a vacuum connection 23 can be seen on the upper side, by means of which the mixing device is connected to a vacuum pump during the mixing of bone cement in order to remove gases and avoid bubble formation.

Figure 7:
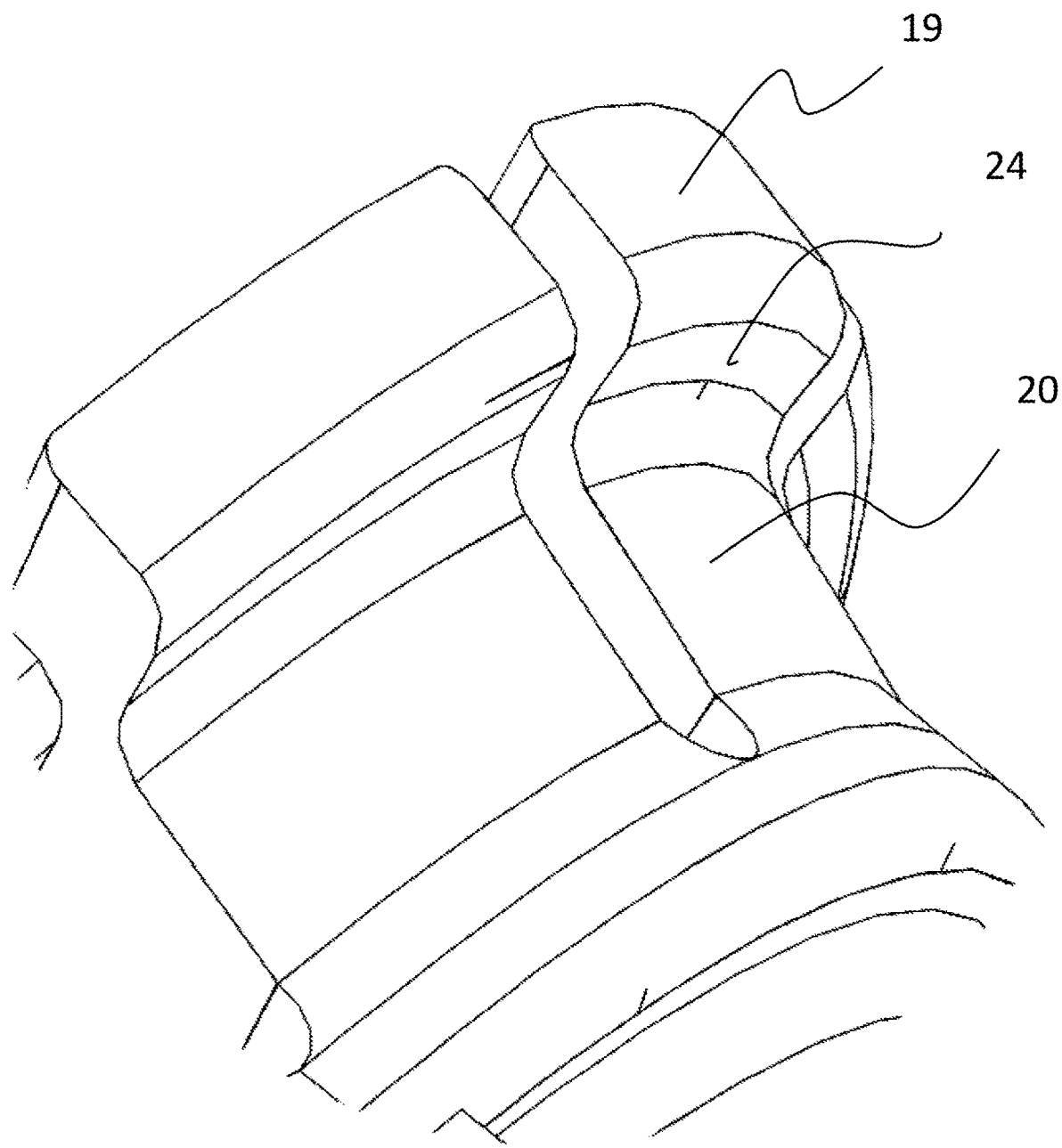
FIG. 7 is a perspective view of a detail of the spring blades of the plunger.

FIG. 7 shows a perspective detailed view of the spring blades of the plunger.

It can be seen that the spring blades have a substantially vertical but slightly inclined spring portion 20 and a hook portion 19 that extends substantially horizontally.

The lower surface of hook portion 19 defines an engagement surface 24 through which the plunger bears on a corresponding support surface of the collar (14 in FIG. 3) when in its cover position.

The transitions of hook portion 19 and spring portion 20 are rounded to allow for better sliding of the L-shaped spring blades.

Figure 8:
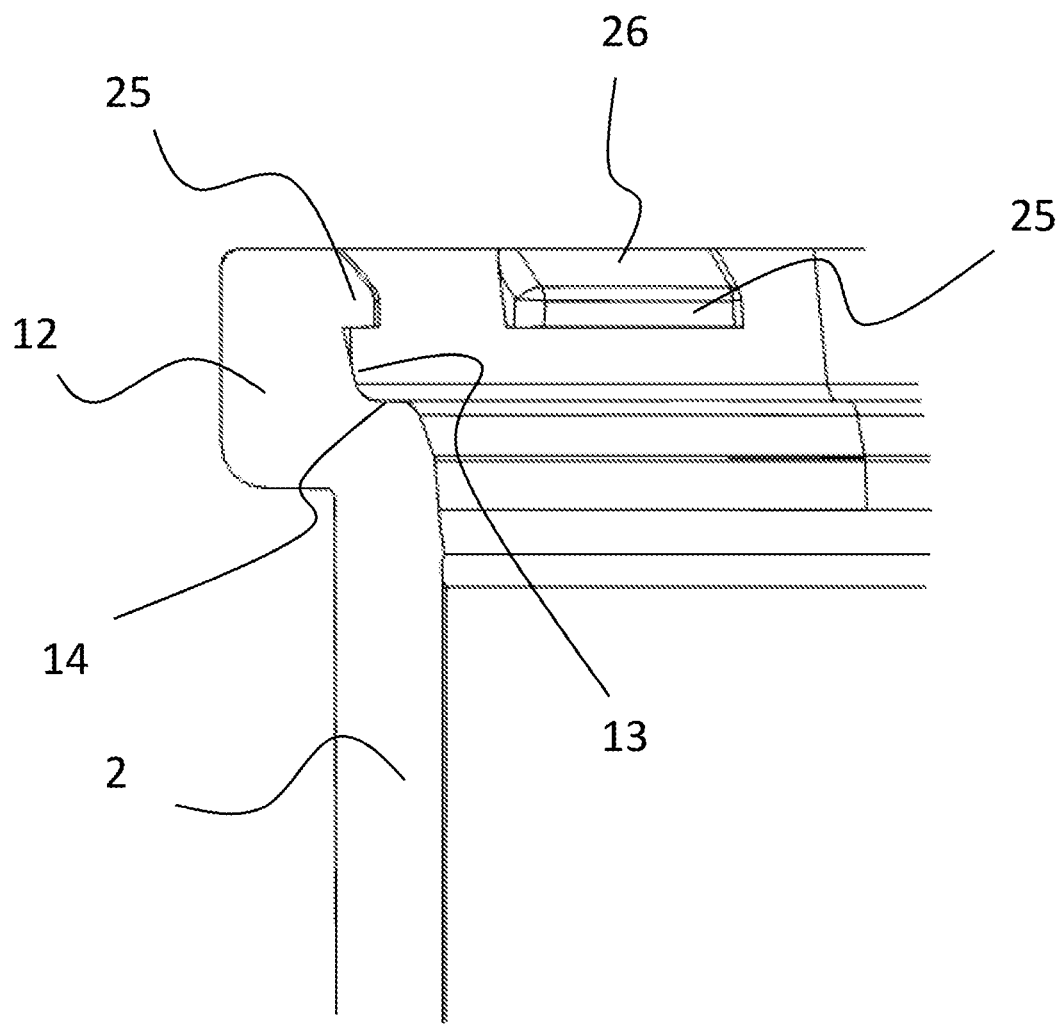
FIG. 8 shows a detail of the collar of the housing.

FIG. 8 shows a detailed view of the collar portion of housing 2.

It can be seen that the collar 12 has locking hooks 25. The upper surface of locking hooks 25 is an inclined surface 26 over which the spring blades slide upon insertion of the plunger.

Then the spring blades will snap below the locking hooks 25, at least partially or in sections, and the plunger will be secured from being axially retracted. At the same time the front side of the spring blades will engage on support surface 14, so that the plunger is locked in its cover position.

The inclined surface 13 can be seen, which facilitates resilient inward deflection of the spring blades when the plunger is advanced.

Locking hooks 25 cover less of the circumference than the spring blades to allow insertion of the plunger with rather low force.

Figure 9:
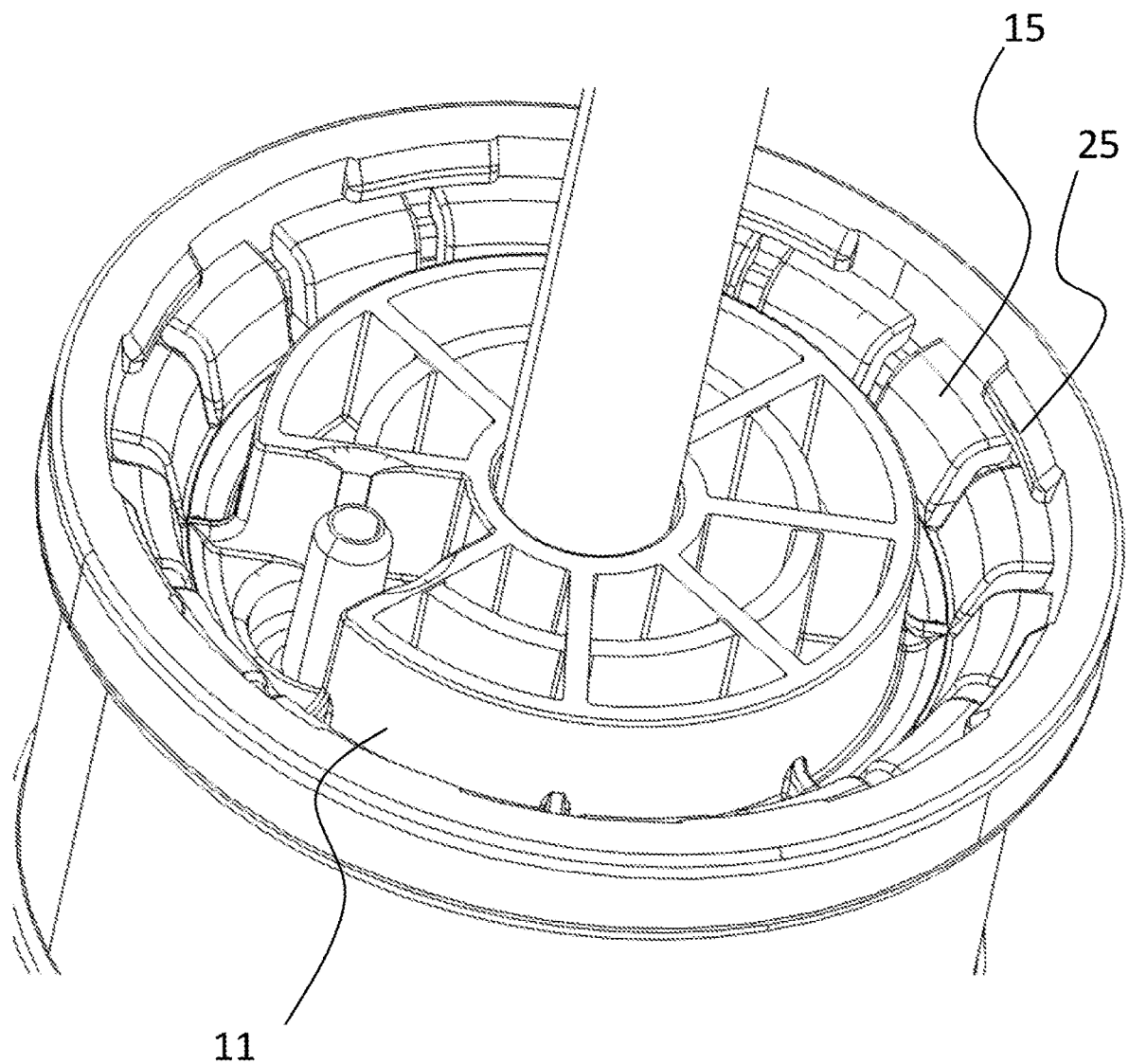
FIG. 9 is a detailed view of the plunger latched in its cover position.

This is particularly apparent in FIG. 9 which shows a perspective view of the latched plunger 11 serving as a cover. Sections of the spring blades 15 are latched under locking hooks 25.

FIG. 10 shows a perspective detail view of the upper part of the mixing device with funnel 3 attached thereto.

Funnel 3 is placed on the housing of the mixing device prior to the assembly of the plunger.

Funnel 3 is divided into two areas, by a partition 27.

The larger area 31 of funnel 3 is intended for introducing the powder component.

The other area 28 is trough-shaped to facilitate filling of a monomer from an ampoule. This area 28 may comprise a sieve to reduce the risk of introducing glass fragments into the mixing cavity. Area 31 for filling the powder component, by contrast, is open above the housing of the mixing device.

Figure 11:
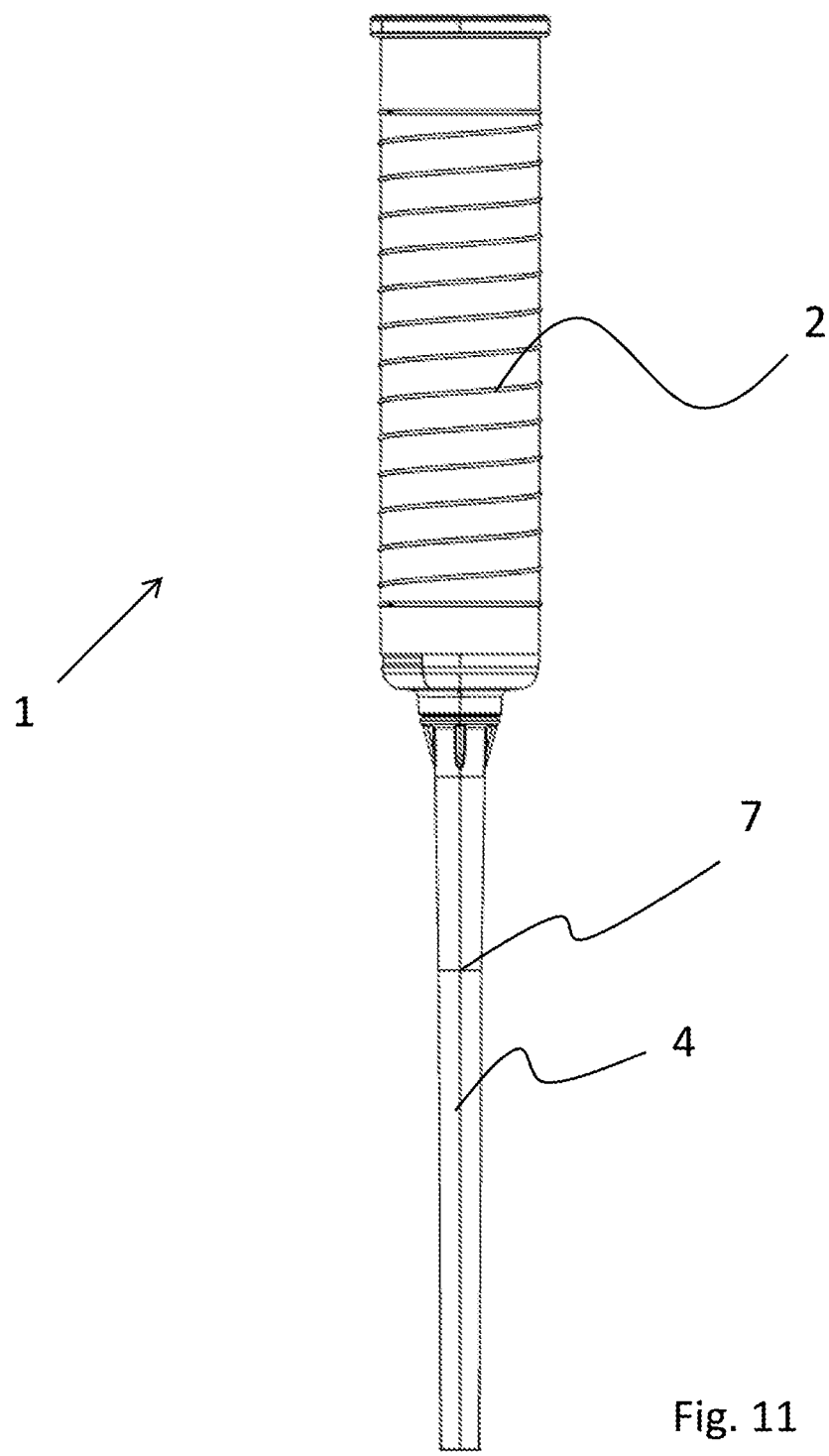
FIG. 11 shows an elevational side view of the mixing device with application tube screwed thereon.

FIG. 11 shows the mixing device 1 before extrusion of the bone cement.

The grip (8 in FIG. 1) was separated together with the rod (10 in FIG. 2) for actuating the mixing paddle. Furthermore, the bottom (5 in FIG. 1) was unscrewed and instead the application tube 4 was mounted on the housing 2. The thread provided for this purpose preferably has a high pitch so that less than one revolution is required for the mounting.

Application tube 4 may have a predetermined breaking point 7 in order to be truncated, depending on the application.

The mixing device illustrated herein is inserted into an applicator gun by means of which the mixed material is forced out.

With the invention it was possible to simplify the handling and assembly and also the manufacturing of a mixing device for bone cement.

LIST OF REFERENCE NUMERALS

1 Mixing device
2 Housing
3 Funnel
4 Application tube
5 Bottom
6 Mixing cavity
7 Predetermined breaking point
8 Grip
9 Mixing paddle
10 Rod
11 Plunger
12 Collar
13 Inclined surface
14 Support surface
15 Spring blades
16 Front portion
17 Seal
18 Groove
19 Hook portion
20 Spring portion
21 Groove
22 Lightweight structure
23 Vacuum connection
24 Engagement surface
25 Locking hooks
26 Sliding surface
27 Partition
28 Trough-shaped area
29 Predetermined breaking point
30 Cut
31 Area for filling the powder component

What is claimed is:

1. A mixing device comprising:
a housing having a mixing cavity and a collar, the collar having an inclined surface that merges with a support surface; and
a plunger adapted to force out mixed material and operative as a housing cover during mixing of the material to be mixed, the plunger having a plurality of spring blades adapted to engage the support surface of the collar to lock the plunger in a cover position, the spring blades each having a spring portion which is inclined outwards relative to a central axis of the plunger, the plurality of spring blades releasing the plunger upon application of a force on the plunger in a forward direction in which the plunger has to be moved to force out the mixed material, the inclined surface of the collar facilitating resilient inward deflection of the spring blades when the force is applied to the plunger, wherein the inclined surface extends vertically and the support surface extends horizontally.

2. The mixing device as claimed in claim 1 wherein the plunger has at least four of the spring blades.

3. The mixing device as claimed in claim 1, wherein the spring blades are formed integrally with the plunger.

4. The mixing device as claimed in claim 1, wherein in a position in the which the plunger serves as a cover, the spring blades are at least partially latched under a locking hook of the housing while an opposite engagement surface thereof engages on a corresponding support surface of the collar.

5. The mixing device as claimed in claim 4, wherein the locking hook has an inclined sliding surface on its upper side.

6. The mixing device as claimed in claim 1, wherein a rod for moving a mixing paddle is guided in the plunger.

7. The mixing device as claimed in claim 1, wherein the spring blades are L-shaped.

8. The mixing device as claimed in claim 1, wherein the plunger comprises a front portion that has an enlarged diameter with respect to a rearward portion.

9. The mixing device as claimed in claim 1, wherein the mixing device comprises a funnel that can be placed on the housing and which is divided into two areas.

10. The mixing device as claimed in claim 9, wherein the mixing device comprises a detachable bottom which can be replaced by an application tube.

11. The mixing device as claimed in claim 1, wherein the spring portion is inclined relative to the central axis of the plunger at an angle between 10° and 60°.

12. The mixing device as claimed in claim 1, wherein said mixing device is filled with bone cement.

13. The mixing device of claim 1, wherein each of the spring blades further has a hook portion that extends outwardly from an upper end of the spring portion.

14. A mixing device comprising:
a housing having a mixing cavity and a collar, the collar having an inclined surface that merges with a support surface; and
a plunger adapted to force out mixed material and operative as a housing cover during mixing of the material to be mixed, the plunger having a plurality of spring blades adapted to engage the support surface of the collar to lock the plunger in a cover position, the spring blades each having a spring portion which is inclined outwards relative to a central axis of the plunger, the plurality of spring blades releasing the plunger upon application of a force on the plunger in a forward direction in which the plunger has to be moved to force out the mixed material, the inclined surface of the collar facilitating resilient inward deflection of the spring blades when the force is applied to the plunger, wherein each of the spring blades further has a hook portion that extends outwardly from an upper end of the spring portion.

\* \* \* \* \*